US008658216B2

(12) United States Patent
Gandhi et al.

(10) Patent No.: US 8,658,216 B2
(45) Date of Patent: Feb. 25, 2014

(54) STABLE ORAL BENZIMIDAZOLE COMPOSITIONS AND PROCESS OF PREPARATION THEREOF

(75) Inventors: Rajesh Gandhi, Haryana (IN); Chayapathy Issa, Andhra Pradesh (IN); Vishnubhotla Nagaprasad, Andhra Pradesh (IN)

(73) Assignee: Ranbaxy Laboratories Limited, New Delhi (IN)

( * ) Notice: Subject to any disclaimer, the term of this patent is extended or adjusted under 35 U.S.C. 154(b) by 1074 days.

(21) Appl. No.: 11/722,731

(22) PCT Filed: Dec. 22, 2005

(86) PCT No.: PCT/IB2005/003858
§ 371 (c)(1),
(2), (4) Date: Feb. 26, 2008

(87) PCT Pub. No.: WO2006/067599
PCT Pub. Date: Jun. 29, 2006

(65) Prior Publication Data
US 2009/0162449 A1    Jun. 25, 2009

(30) Foreign Application Priority Data
Dec. 23, 2004    (IN) .......................... 2551/DEL/2004

(51) Int. Cl.
*A61K 9/16*    (2006.01)

(52) U.S. Cl.
USPC .......................................................... 424/494

(58) Field of Classification Search
USPC .......................................................... 424/494
See application file for complete search history.

(56) References Cited

U.S. PATENT DOCUMENTS

| 4,255,431 | A | 3/1981 | Junggren et al. ............... 424/263 |
| 4,738,974 | A | 4/1988 | Brändström ................... 514/338 |
| 4,786,505 | A | 11/1988 | Lovgren et al. ............... 424/468 |
| 4,853,230 | A | 8/1989 | Lovgren et al. ............... 424/466 |
| 5,385,739 | A | 1/1995 | Debregeas et al. ............ 424/494 |
| 5,626,875 | A | 5/1997 | Ballester Rodes et al. ..... 424/464 |
| 5,690,960 | A | 11/1997 | Bengtsson et al. ............ 424/480 |
| 5,877,192 | A | 3/1999 | Lindberg et al. .............. 514/338 |
| 5,900,424 | A | 5/1999 | Källström et al. ............. 514/338 |
| 6,159,499 | A | 12/2000 | Seth .............................. 424/451 |
| 6,207,198 | B1 | 3/2001 | Seth .............................. 424/494 |
| 6,274,173 | B1 | 8/2001 | Sachs et al. ................... 424/480 |
| 6,564,113 | B1 * | 5/2003 | Barto et al. ..................... 700/99 |
| 6,602,522 | B1 | 8/2003 | Chen et al. .................... 424/480 |
| 6,713,495 | B1 | 3/2004 | Sherman ....................... 514/338 |
| 2002/0128293 | A1 | 9/2002 | Rampal et al. ................ 514/338 |
| 2003/0232861 | A1 | 12/2003 | Sherman ....................... 514/338 |

FOREIGN PATENT DOCUMENTS

| CA | 2502219 | 4/2004 | ........ A61K 31/4439 |
| IN | 1494/DEL/2003 | 11/2003 | |
| WO | WO 2004/002982 | 1/2004 | ........... C07D 401/00 |
| WO | WO 2004/037253 | 5/2004 | ........ A61K 31/4439 |
| WO | WO 2004/066982 | 8/2004 | ............... A61K 9/30 |
| WO | WO 2006/002077 | 1/2006 | ............... A61K 9/00 |

OTHER PUBLICATIONS

Sorasuchart (Drug Release from Spray Layered and Coated Drug-Containing Beads: Effects of pH and Comparison of Different Dissolution Methods, Drug Development and Industrial Pharmacy, vol. 25, No. 10, pp. 1093-1098, 1999).*

* cited by examiner

*Primary Examiner* — Frederick Krass
*Assistant Examiner* — Adam C Milligan

(57) ABSTRACT

The present invention relates to stable oral compositions of one or more benzimidazole compounds and processes for their preparation. Also provided are methods for treating various gastrointestinal disorders.

15 Claims, No Drawings

STABLE ORAL BENZIMIDAZOLE COMPOSITIONS AND PROCESS OF PREPARATION THEREOF

TECHNICAL FIELD OF THE INVENTION

The present invention relates to stable oral compositions of one or more benzimidazole compounds and processes for the preparation thereof. Also provided are methods for treating various gastrointestinal disorders.

BACKGROUND OF THE INVENTION

Benzimidazole compounds, such as omeprazole, lansoprazole, pantoprazole, rabeprazole or single enantiomers thereof are strong inhibitors of proton pump and are widely used as therapeutic agents for stomach ulcer, duodenal ulcer, and gastro esophageal reflux disorders. Benzimidazole compounds effectively inhibit gastric acid secretion.

U.S. Pat. No. 4,255,431 discloses omeprazole and therapeutically acceptable salts thereof. U.S. Pat. No. 4,738,974 specifically discloses, among other salts, the magnesium salt of omeprazole Efforts to stabailize benzimidazole compositions using amorphous form of benzimidazole compounds are reported in literature. WO 04/037253 and WO 04/002982 teach processes of preparing amorphous forms of a salt of esomeprazole.

U.S. Pat. No. 6,713,495 discloses magnesium omeprazole having a degree of crystallinity of under 67% by weight and having a residual organic solvent content of less than 7% by weight. U.S. Patent. Application No. 2003/0232861 discloses magnesium s-omeprazole having a degree of crystallinity of under 67%. Example 3 of U.S. Pat. No. 6,713,495 and U.S. patent application No. 2003/0232861 disclose magnesium omeprazole and magnesium esomeprazole respectively, having a degree of crystallinity under 25%.

Indian application no. 1494/DEL/2003, discloses stable oral benzimidazole compositions. The compositions include a core comprising amorphous or crystalline benzimidazole compound, a substantially water-insoluble and substantially non-disintegrating separating layer and an enteric coating.

U.S. Patent Application No. 2002/0128293 teaches stable oral pharmaceutical compositions that include omeprazole and a stabilizing excipient, wherein the composition is free of alkaline compounds. Example 7 of the patent application discloses a process of wet drug layering of an inert carrier using a Wurster fluid bed apparatus.

Because of the strong tendency of benzimidazole compounds to decompose in a neutral and in particular, acidic environment, numerous approaches have been tried to form a stable pharmaceutical formulation comprising such compounds. The acid labile benzimidazole compounds react with both the gastric acid in the stomach and the enteric coatings used for preventing the benzimidazole from coming into contact with the gastric acid.

U.S. Pat. Nos. 6,274,173, 6,602,522, 5,385,739, 5,626,875, 6,159,499, 6,207,198, 5,900,124, 5,877,192, 5,690,960, 4,786,505, and 4,853,230 disclose various approaches to formulate benzimidazole compositions.

There still is a need for the development of oral pharmaceutical compositions of benzimidazole compounds which are stable, as defined herein, during formulation and storage. It has surprisingly been found that careful control of some of the processing parameters is critical to prevent the conversion of the amorphous form of benzimidazole compound to the crystalline form.

The present invention thus relates to the stable oral amorphous benzimidazole compositions and process for preparing the same as herein below described and exemplified.

SUMMARY OF THE INVENTION

In one general aspect there is provided a stable oral benzimidazole composition comprising a benzimidazole core in the form of bead, the core comprising a pharmaceutically acceptable inert carrier coated with one or more amorphous benzimidazole compounds and one or more pharmaceutically acceptable additives; a separating layer surrounding the core; and an enteric coating surrounding the separating layer, wherein the composition contains less than about 30% weight of crystalline benzimidazole.

Embodiments of the present invention may include one or more of the following features. For example, the benzimidazole compound may be one or more of omeprazole, lansoprazole, rabeprazole, pantoprazole, leminoprazole, pariprazole, their single enantiomers, pharmaceutically accepted salts, solvates or mixtures thereof.

The pharmaceutically acceptable additive may include one or more of binders, diluents, disintegrants, lubricants and wetting agents. The binder may be one or more of cellulose derivatives, gums, water-soluble vinylpyrrolidone polymers, and sugars. The diluent may be one or more of sugars, sugar alcohols, cellulose derivatives, and starches. The disintegrant may be one or more of sodium starch glycolate, croscarmellose sodium, crospovidone, corn starch and mixtures thereof. The lubricant may be one or more of magnesium stearate, talc, sodium stearyl fumarate, colloidal silicon dioxide and mixtures thereof. The wetting agent may be one or more of sodium lauryl sulphate, polysorbate 80 and mixtures thereof.

The separating layer may include a substantially water-soluble material. The substantially water-soluble material may be one or more of a substantially water-soluble polymer and a substantially water-soluble excipient. The water-soluble polymer may be one or more of hydroxypropyl methylcellulose, hydroxypropyl cellulose, polyvinylpyrrolidone, sodium alginate, sodium carboxymethyl cellulose, copolymer of vinylpyrrolidone and vinyl acetate. The water-soluble excipient may be one or more of lactose, mannitol, sorbitol, sucrose and glucose.

In another general aspect there is provided a process for the preparation of a stable oral benzimidazole composition. The process includes the steps of:
a) preparing a benzimidazole core formed by dispersing one or more amorphous benzimidazole compounds and one or more pharmaceutically acceptable additives in an aqueous or hydroalcoholic medium to obtain a dispersion;
b) spraying the dispersion onto a pharmaceutically acceptable inert carrier;
c) coating the core with a separating layer; and
d) coating the product of step (b) with an enteric coating, wherein the process of preparation of the benzimidazole core substantially prevents the conversion of benzimidazole compound to its crystalline form.

Embodiments of the process may include one or more of the following features. For example, step (a) may include spraying the dispersion on the pharmaceutically acceptable inert carrier at a bed temperature of less than about 50° C. Step (a) may include spraying the dispersion on the pharmaceutically acceptable inert carrier, such that the total spraying time is less than about 24 hrs. The dispersion of step (a) may be prepared in more than one lot.

The one or more benzimidazole compounds may include one or more of omeprazole, lansoprazole, rabeprazole, pantoprazole, leminoprazole, pariprazole, single enantiomers, pharmaceutically accepted salts, solvates or mixtures thereof. The pharmaceutically acceptable additive may include one or more of binders, diluents, disintegrants, lubricants and wetting agents. The separating layer may include a substantially water-soluble material.

In another general aspect there is provided a method of inhibiting gastric acid secretion in a patent in need thereof. The method includes administering to a patient in need thereof a stable oral benzimidazole composition comprising:
  a. a benzimidazole core in the form of bead, the core comprising an pharmaceutically acceptable inert carrier coated with one or more amorphous benzimidazole compound and one or more pharmaceutically acceptable additives;
  b. a separating layer surrounding the core; and
  c. an enteric coating surrounding the separating layer, wherein the composition contains less than about 30% by weight of crystalline benzimidazole.

DETAILED DESCRIPTION OF THE INVENTION

The term 'benzimidazole compound' as used herein refers to any of the compounds belonging to the category of benzimidazole used for gastrointestinal disorders and may include one or more of omeprazole, lansoprazole, rabeprazole, pantoprazole, leminoprazole, pariprazole, single enantiomers, pharmaceutically accepted salts, solvates or mixtures thereof. Preferably, the benzimidazole compound may be omeprazole in the form of a pharmaceutically acceptable alkaline salt. More preferably, omeprazole may be in the form of omeprazole magnesium or esomeprazole magnesium. Preferably, the benzimidazole compound is in substantially amorphous form.

The term 'substantially amorphous' refers to having less than 30% crystalline compound by weight. Amorphous esomeprazole magnesium may be prepared according to PCT Application nos. 04/037253 and 04/002982, both of which are herein incorporated by reference. However any other suitable method can be used to prepare amorphous esomeprazole magnesium used in the present invention.

The term 'stable oral composition' as used herein refers to the oral compositions of amorphous benzimidazole compounds, which are substantially free from crystalline benzimidazole. Preferably, the stable oral composition contains not more than 30% by weight of crystalline benzimidazole. X-ray powder diffraction can be used for determining the content of the crystalline form in the compositions of present invention with substantial precision.

The term 'benzimidazole core' as used herein includes one or more benzimidazole compounds and one or more pharmaceutically acceptable additives which are substantially free from crystalline benzimidazole. Preferably, the benzimidazole core contains not more than 30% by weight of crystalline benzimidazole. The benzimidazole core is prepared under optimized processing conditions in order to prevent the conversion of amorphous benzimidazole to crystalline benzimidazole. Preferably, the conversion to crystalline benzimidazole is less than about 30% by weight. The benzimidazole core may be obtained in the form of granules, pellets, beads or minitablets, which may be further processed to obtain benzimidazole compositions in suitable dosage form. For example, the benzimidazole core may be coated with a separating layer and an enteric coating to obtain a coated core. The coated core may be filled into capsules or compressed into tablets.

The term 'composition' refers to any oral dosage form such as tablet or capsule, comprising the benzimidazole core.

The 'pharmaceutically acceptable additives' may include one or more of binders, diluents, disintegrants, lubricants/glidants and solubilizers/wetting agents.

Suitable diluents may include one or more sugars, such as dextrose, glucose, lactose; sugar alcohols, such as sorbitol, xylitol, mannitol; cellulose derivatives, such as powdered cellulose, microcrystalline cellulose; starches, such as corn starch, pregelatinized starch, or maize starch. The preferred range of diluents depends on the type of composition to be prepared. Some preferred ranges are disclosed in the corresponding examples.

Suitable binders include one or more of cellulose derivatives, such as hydroxypropylmethyl cellulose, hydroxypropyl cellulose, methylcellulose; gums, such as xanthan gum, gum acacia, tragacanth; water-soluble vinylpyrrolidone polymers, such as polyvinylpyrrolidone, copolymer of vinylpyrrolidone and vinyl acetate; sugars, such as sorbitol, mannitol and mixtures thereof. The preferred range of binders depends on the type of composition to be prepared. Some preferred ranges are disclosed in the corresponding examples.

Generally the disintegrants are selected from sodium starch glycolate, croscarmellose sodium, crospovidone, cornstarch or mixtures thereof. The preferred range of disintegrants depends on the type of composition to be prepared. The preferred range is disclosed in the corresponding examples.

Suitable solubilizers/wetting agents may include one or more of sodium lauryl sulphate, polysorbate 80 or mixtures thereof. The lubricant/glidants may include one or more of magnesium stearate, talc, sodium stearyl fumarate, colloidal silicon dioxide and mixtures thereof.

The benzimidazole core is prepared using an optimized process in order to prevent the conversion to crystalline benzimidazole. The one or more amorphous benzimidazole compounds and one or more pharmaceutically acceptable additives may be dispersed in an aqueous or hydroalcoholic medium to obtain a dispersion. The resulting dispersion may be sprayed on a pharmaceutically acceptable inert carrier in a fluidized bed apparatus, e.g., Wurster coater. The process parameters during the drug loading process should be maintained to prevent the conversion to crystalline benzimidazole compound. The important process parameters include the benzimidazole dispersion media, the total solid content in the dispersion, the total spraying time for the preparation of the benzimidazole core, the number of prepared lots of the dispersion, the inlet temperature and the bed temperature during the preparation of the benzimidazole core, the drying temperature, the ratio of omeprazole to the additive in dispersion and such like. Particularly, the inlet temperature and the resulting bed temperature maintained during the preparation of the benzimidazole core are found to be important. The following conditions, maintained during the preparation of the core, were found suitable for preparing compositions of the present invention:

Dispersion media—Aqueous or hydroalcohlic
  Total solid content in dispersion—5-20% w/w
  Total spraying time for the preparation of benzimidazole core—not more than 24 h.
  Number of prepared lots of dispersion—more than 1
  Bed Temperature during preparation of benzimidazole core—not more than 50° C.
  Drying Temperature—not more than 50° C.
  Benzimidazole to binder ratio in dispersion—from about 10:1 to about 1:5
  Benzimidazole to disintegrant ratio in dispersion—from about 10:1 to about 1:10

The benzimidazole core may also be prepared using a rotor granulator, wherein a mixture comprising amorphous benzimidazole compound and one or more pharmaceutically acceptable additives together with a binder dispersion is sprayed on to a pharmaceutically acceptable inert carrier in a rotor granulator under optimized processing conditions. Alternatively, the amorphous benzimidazole compound may be mixed with pharmaceutically acceptable additive and processed using wet granulation/dry granulation.

The 'pharmaceutically acceptable inert carrier' may include a starch, microcrystalline cellulose or sugar sphere, such as nonpareil sugar seeds.

The separating layer as used herein refers to the layer that separates the core from the enteric coating. The separating layer is made up of substantially water soluble material which is capable of dissolving or forming a gel in contact with water. Such material may include substantially water-soluble polymer and/or substantially water-soluble excipients. In the case when the capsule shell acts as a separating layer, additional application of separating layer would be optional. The enteric coating can directly be layered on the capsule shell in such case.

The substantially water-soluble excipients may include one or more of glucose, lactose, mannitol, sorbitol, sucrose, dextrose and mixtures thereof. The substantially water-soluble polymers may include hydroxypropylmethylcellulose, hydroxypropyl cellulose, polyvinylpyrrolidone, sodium alginate, sodium carboxymethyl cellulose, copolymer of vinylpyrrolidone and vinyl acetate. Preferably, the polymers may be hydroxypropylmethylcellulose, hydroxypropyl cellulose or polyvinylpyrrolidone. The range of such substantially water-soluble polymers depends on the type of compositions to be prepared.

The enteric coating may include polymers, such as cellulose acetate phthalate, hydroxypropyhnethyl cellulose phthalate, polyvinyl acetate phthalate, carboxymethylethylcellulose, methacrylic acid copolymers, such as, compounds known under the trademarks of Eudragit NE30D, Eudragit L, Eudragit S, Eudragit L 100 55 or mixtures thereof. The enteric coating may also include plasticizers, such as triacetin, triethyl citrate, tributyl sebecate, diethyl phthalate, polyethylene glycol and inert excipients such as talc, titanium dioxide, colloidal silicon dioxide, hydroxypropyl methylcellulose, crospovidone and mixtures thereof.

The compositions of the present invention show that they remained substantially amorphous under storage at 40° C. and 75% humidity conditions for a period of at least 1 month, preferably 3 months, more preferably 6 months, as determined by X ray powder diffraction.

While the present invention has been described in terms specific to those skilled in the art and are included within the scope of the present invention, the following examples are provided to illustrate particular aspects on the disclosure and do not limit the scope of the present invention as defined by the claims.

EXAMPLE 1

| S. No | Ingredients | Quantity (mg/capsule) 1A | 1B | 1C |
|---|---|---|---|---|
| A) | Benzimidazole core | | | |
| 1 | Non-pareil seeds (20-25) | 100.0 | 100.0 | 60.0 |
| 2 | Amorphous esomeprazole magnesium | 44.5 | 44.5 | — |
| 3 | Amorphous omeprazole magnesium | — | — | 20.6 |
| 4 | Hydroxypropylmethylcellulose | — | 20.0 | 5.0 |
| 5 | Hydroxypropyl cellulose (HPC-L) | 20.0 | — | 5.0 |
| 6 | Crospovidone (Kollidon CLM) | 30.0 | 30.0 | — |
| 7 | Purified water | qs | qs | qs |
| B) | Separating layer | | | |
| 1 | Hydroxypropyl methylcellulose (HPMC) 5 cps | 14.98 | — | 6.97 |
| 2 | Hydroxypropyl cellulose | — | 14.98 | — |
| 3 | Polyethylene glycol 400 | 1.49 | 1.49 | 0.69 |
| 4 | Talc | 2.98 | 2.98 | 1.4 |
| 5 | Purified water | qs | qs | qs |
| C) | Enteric coat | | | |
| 1 | Methacrylic Acid Copolymer Type C | 39.76 | 39.76 | 18.7 |
| 2 | Polyethylene glycol 400 | 3.98 | — | 1.87 |
| 3 | Triethyl citrate | — | 3.98 | — |
| 4 | Talc | 15.11 | 15.11 | 7.1 |
| 5 | Titanium dioxide | 4.7 | 2.7 | 2.22 |
| 6 | Purified water | qs | qs | qs |
| D) | Lubrication | | | |
| 1 | Talc | 0.50 | 0.50 | 0.45 |
| | Total | 278.0 | 276.0 | 130.0 |

Process

A. Preparation of Benzimidazole Core
1. Hydroxypropyl cellulose/hydroxypropylmethylcellulose was dissolved in purified water under mechanical stirring followed by addition of crospovidone and amorphous esomeprazole magnesium/amorphous omeprazole magnesium to obtain a dispersion.
2. The dispersion (prepared in four lots) was sprayed on non-pareil seeds in a Wurster coater during 12-24 h using the following parameters, while continuing the slow stirring of the dispersion:
   Inlet air temperature: 45-60° C.
   Bed temperature: 35-40° C.
   Pump rpm: 15-25
   Atomisation air pressure: 2.0-5.0 kg/cm$^2$
3. The material of step 2 above was dried at 35-40° C. till the loss on drying is less than 1.5% w/w to obtain the benzimidazole core.

B. Separating Layer
1. Hydroxypropyl methylcellulose/hydroxypropylcellulose were dissolved in purified water under mechanical stirring followed by addition of polyethylene glycol and talc to obtain a coating dispersion.
2. The coating dispersion was sprayed on the benzimidazole core in a Wurster coater using the following parameters, while continuing the slow stirring of the dispersion:
   Inlet air temperature: 45-60° C.
   Bed temperature: 35-40° C.
   Pump rpm: 10-20
   Atomisation air pressure: 2.0-5.0 kg/cm$^2$
3. The coated core of step 2 above was dried at 35-40° C. for 15 minutes to obtain the coated benzimidazole core.

C. Enteric Coating
1. Polyethylene glycol/triethyl citrate were dissolved in purified water under mechanical stirring followed by addition of titanium dioxide and talc to obtain a dispersion.
2. Methacrylic acid copolymer type C was added to the dispersion of step 1 under mechanical stirring to obtain a coating dispersion.
3. The coating dispersion of step 2 was sprayed on the coated benzimidazole core in Wurster coater using the following parameters, while continuing the slow stirring of the dispersion:

Inlet air temperature: 40-50° C.
Bed temperature: 30-35° C.
Pump rpm: 10-20
Atomisation air pressure: 2.0-5.0 kg/cm$^2$
4. The coated core of step 3 above was dried at 35-40° C. for 15 minutes to obtain the enteric coated benzimidazole core.
D. Lubrication
1. The enteric coated benzimidazole core was fluidized with talc in a Wurster coater for 5 minutes.
2. The core of step 1 above was dried in a vacuum tray drier at 40° C. till the loss on drying is less than 1.5% w/w.

The XRD data indicated that the content of crystalline omeprazole/esomeprazole magnesium in 1A, 1B and 1C is less than 5% by weight.

Example 2

| S. No | Ingredients | 2A | 2B (Reference example) |
|---|---|---|---|
| | | Quantity (mg/capsule) | |
| A) | Benzimidazole core | | |
| 1 | Non-pareil seeds (20-25) | 100.0 | 100.0 |
| 2 | Amorphous esomeprazole magnesium | 44.5 | 44.5 |
| 3 | Hydroxypropyl cellulose (HPC-L) | 20.0 | 20.0 |
| 4 | Crospovidone (Kollidon CLM) | 30.0 | 30.0 |
| 5 | Purified water | qs | qs |
| B) | Separating layer | | |
| 1 | Hydroxypropyl methylcellulose (HPMC) 5 cps | 14.98 | 14.98 |
| 2 | Polyethylene glycol 400 | 1.49 | 1.49 |
| 3 | Talc | 2.98 | 2.98 |
| 4 | Purified water | qs | qs |
| C) | Enteric coat | | |
| 1 | Methacrylic acid copolymer Type C | 39.76 | 39.76 |
| 2 | Polyethylene glycol 400 | 3.98 | 3.98 |
| 3 | Talc | 15.11 | 15.11 |
| 4 | Titanium dioxide | 4.7 | 4.7 |
| 5 | Purified water | qs | qs |
| D) | Lubrication | | |
| 1 | Talc | 0.50 | 0.50 |
| | Total | 278.0 | 278.0 |

Process
A. Preparation of Benzimidazole Core
A procedure similar to Example 1 above was followed except for the following process parameters:

Example 2A

Inlet air temperature: 50-70° C.
Bed temperature: 40-50° C.
Pump rpm: 15-25
Atomisation air pressure: 2.0-5.0 kg/cm$^2$ Reference Example 2B Inlet air temperature: 70-80° C.
Bed temperature: 51-60° C.
Pump rpm: 15-25
Atomisation air pressure: 2.0-5.0 kg/cm$^2$
C. Separating Layer
A procedure similar to Example 1 above was followed.
C. Enteric Coating
A procedure similar to Example 1 above was followed.
D. Lubrication
A procedure similar to Example 1 above was followed.

The XRD data indicated that the content if crystalline esomeprazole magnesium to be 15-30% by weight for Example 2A and 65-100% by weight for Example 2B.

Reference Example 3

The composition was the same as Example 1A and was prepared by using a process similar to Example 1A except that the total spraying time for the preparation of the benzimidazole core was greater than 24 h. The XRD data indicated that the content of crystalline esomeprazole magnesium to be 65-100% by weight.

Example 4

| S. No | Ingredients | 4A | 4B (Reference example) |
|---|---|---|---|
| | | Quantity (mg/capsule) | |
| A) | Benzimidazole core | | |
| 1 | Non-pareil seeds (20-25) | 100.0 | 100.0 |
| 2 | Amorphous esomeprazole magnesium | 44.5 | 44.5 |
| 3 | Amorphous omeprazole magnesium | — | — |
| 4 | Hydroxypropylmethylcellulose | — | — |
| 5 | Hydroxypropyl cellulose (HPC-L) | 20.0 | 20.0 |
| 6 | Crospovidone (Kollidon CLM) | 30.0 | 30.0 |
| 7 | Purified water | qs | Qs |
| B) | Separating layer | | |
| 1 | Hydroxypropyl methylcellulose (HPMC) 5 cps | 14.98 | 14.98 |
| 2 | Hydroxypropyl cellulose | — | — |
| 3 | Polyethylene glycol 400 | 1.49 | 1.49 |
| 4 | Talc | 2.98 | 2.98 |
| 5 | Purified water | qs | Qs |
| C) | Enteric coat | | |
| 1 | Methacrylic Acid Copolymer Type C | 39.76 | 39.76 |
| 2 | Polyethylene glycol 400 | 3.98 | 3.98 |
| 3 | Triethyl citrate | — | — |
| 4 | Talc | 15.11 | 15.11 |
| 5 | Titanium dioxide | 4.7 | 4.7 |
| 6 | Purified water | qs | Qs |
| D) | Lubrication | | |
| 1 | Talc | 0.50 | 0.50 |
| | Total | 278.0 | 278.0 |

Process

A process similar to Example 1A was followed except that during the preparation of the benzimidazole core the dispersion was prepared in 2 lots (4A) and 1 lot (Reference Example 4B) and the total spraying time was 24-36 hrs. The XRD data indicated that the content of crystalline esomeprazole magnesium to be 15-30% by weight for Example 4A and 65-100% by weight for Example 4B.

Example 5

| S. No | Ingredients | Quantity (mg/capsule) |
|---|---|---|
| A) | Benzimidazole core | |
| 1 | Non-pareil seeds (20-25) | 100.0 |
| 2 | Amorphous esomeprazole magnesium | 44.5 |
| 3 | Hydroxypropyl cellulose (HPC-L) | 20.0 |
| 4 | Crospovidone (Kollidon CLM) | 30.0 |
| 5 | Purified water | qs |

-continued

| S. No | Ingredients | Quantity (mg/capsule) |
|---|---|---|
| B) | Separating layer | |
| 1 | Hydroxypropyl methylcellulose (HPMC) 5 cps | 14.98 |
| 2 | Polyethylene glycol 400 | 1.49 |
| 3 | Talc | 2.98 |
| 4 | Purified water | qs |
| C) | Enteric coat | |
| 1 | Methacrylic Acid Copolymer Dispersion (Eudragit L30D 55) equivalent to dry polymer | 28.11 |
| 2 | Polyethylene glycol 400 | 2.81 |
| 3 | Talc | 10.39 |
| 4 | Titanium dioxide | 3.32 |
| 5 | Purified water | qs |
| D) | Lubrication | |
| 1 | Talc | 0.42 |
| | Total | 259.0 |

Process

A. Preparation of Benzimidazole Core

1. Hydroxypropyl cellulose was dissolved in purified water under mechanical stirring followed by addition of crospovidone and amorphous esomeprazole magnesium to obtain a dispersion.
2. The dispersion (prepared in six lots) was sprayed on non-pareil seeds in a Wurster coater during 12-24 hrs to achieve weight buildup of approximately 94.5% using the following parameters, while continuing the slow stirring of the dispersion:
    Inlet air temperature: 45-60° C.
    Bed temperature: 35-40° C.
    Pump rpm: 15-25
    Atomisation air pressure: 2.0-5.0 kg/cm$^2$
3. The material of step 2 above was dried at 35±5° C. for 15-30 minutes to obtain the benzimidazole core.

B. Separating Layer

1. Hydroxypropyl methylcellulose was dissolved in purified water under mechanical stirring followed by addition of polyethylene glycol and talc to obtain a coating dispersion.
2. The coating dispersion was sprayed on the benzimidazole core in a Wurster coater to achieve a weight build up of approximately 10% using the following parameters, while continuing the slow stirring of the dispersion:
    Inlet air temperature: 45-60° C.
    Bed temperature: 35-40° C.
    Pump rpm: 10-20
    Atomisation air pressure: 2.0-5.0 kg/cm$^2$
3. The coated core of step 2 above was dried at 35±5° C. for 15-30 minutes to obtain the coated benzimidazole core.

C. Enteric Coating

1. Polyethylene glycol was dissolved in purified water under mechanical stirring followed by addition of titanium dioxide and talc to obtain a dispersion.
2. Methacrylic acid copolymer dispersion was added to the dispersion of step 1 under mechanical stirring to obtain a coating dispersion.
3. The coating dispersion of step 2 was sprayed on the coated benzimidazole core in a Wurster coater to achieve a weight build up of approximately 25% using the following parameters, while continuing the slow stirring of the dispersion:
    Inlet air temperature: 40-50° C.
    Bed temperature: 30-35° C.
    Pump rpm: 10-20
    Atomisation air pressure: 2.0-5.0 kg/cm$^2$
4. The coated core of step 3 above was dried at 30-35° C. for 15-30 minutes to obtain the enteric coated benzimidazole core.

D. Lubrication

1. The enteric coated benzimidazole core was fluidized with talc in a Wurster coater for 3-5 minutes.
2. The core of step 1 above was dried in a vacuum tray drier at 40° C. till the loss on drying is less than 1.5% w/w.

The XRD data indicated that the content of crystalline esomeprazole magnesium to be less than 5% by weight. The XRD data of the composition after storage at 40° C. and 75% RH for 3 months indicated that the content of crystalline esomeprazole magnesium remained less than 5% by weight.

Example 6

| S. No | Ingredients | Quantity (mg/capsule) |
|---|---|---|
| A) | Benzimidazole core | |
| 1 | Amorphous esomeprazole magnesium | 44.5 |
| 2 | Lactose monohydrate | 84.30 |
| 3 | Microcrystalline cellulose | 15.0 |
| 4 | Crospovidone Part A | 10.0 |
| 5 | Hydroxypropyl methylcellulose | 8.0 |
| 6 | Sodium lauryl sulphate | 1.2 |
| 7 | Purified water | qs |
| 8 | Crospovidone Part B | 8.0 |
| 9 | Microcrystalline cellulose (Avicel PH112) | 24.0 |
| 10 | Talc | 2.0 |
| 11 | Sodium stearyl fumarate | 3.0 |
| B) | Separating layer | |
| 1 | Hydroxypropyl methylcellulose | 10.78 |
| 2 | Polyethylene glycol | 1.09 |
| 3 | Talc | 2.13 |
| 4 | Purified water | qs |
| C) | Enteric coat | |
| 1 | Eudragit L30D-55# | 301.33 |
| 2 | Triethyl citrate | 23.13 |
| 3 | Talc | 2.71 |
| 4 | Titanium dioxide | 8.74 |
| 5 | Purified water | qs |
| | Total | 255.5 |

30% w/w aqueous dispersion

Process

A. Preparation of Benzimidazole Core

1. Amorphous esomeprazole magnesium, lactose monohydrate, microcrystalline cellulose, crospovidone (part A) and hydroxypropyl methylcellulose were blended in a Rapid mixer granulator to obtain a blend.
2. Sodium lauryl sulphate was dissolved in purified water to obtain a solution.
3. The blend of step 1 was granulated using the solution of step 2 followed by drying in a fluid bed drier at 40° C. for 4 hrs and sifting to obtain granules.
4. The granules of step 3 were blended with microcrystalline cellulose (Avicel PH112), crospovidone part B, talc and sodium stearyl fumarate to obtain a final blend.
5. The final blend of step 4 was compressed into mini tablets using a rotary tablet compression machine to obtain benzimidazole core.

B. Separating Layer

1. Hydroxypropyl methylcellulose was dissolved in purified water under mechanical stirring followed by addition of polyethylene glycol and talc to obtain a coating dispersion.
2. The coating dispersion was sprayed on the benzimidazole core in a perforated coating pan using the following parameters, while continuing the slow stirring of the dispersion:

Inlet air temperature: 40-45° C.
Bed temperature: 35-38° C.
Pan speed rpm: 10-24
Pump rpm: 6-8
Atomisation air pressure: 2.0-4.0 kg/cm$^2$ C. Enteric Coating
1. Triethyl citrate was dissolved in purified water under mechanical stirring followed by addition of titanium dioxide and talc to obtain a dispersion.
2. Eudragit L30D-55 was added to the dispersion of step 1 under mechanical stirring to obtain a coating dispersion.
3. The coating dispersion of step 2 was sprayed on the coated benzimidazole core in a perforated coating pan using the following parameters, while continuing the slow stirring of the dispersion:

Inlet air temperature: 35-40° C.
Bed temperature: 32-35° C.
Pan speed rpm: 10-24
Pump rpm: 6-15
Atomisation air pressure: 2.0-4.0 kg/cm$^2$ The XRD data indicated that the content of crystalline esomeprazole magnesium to be less than 5% by weight.

The following table shows the effect of various process parameters on the conversion of amorphous benzimidazole to crystalline form.

| 1 | Processing bed temperature | | | |
|---|---|---|---|---|
| | Example No. | 1A-1C | 2A | 2B |
| | Bed temperature | 35-40° C. | 40-50° C. | 51-60° C. |
| | % crystalline | <5% | 15-30% | 65-100% |
| 2 | Number of lots of dispersion | | | |
| | Example No. | 1A-1C | 4A | 4B |
| | No. of lots | 4 | 2 | 1 |
| | % crystalline | <5% | 15-30% | 65-100% |
| 3 | Total spraying time | | | |
| | Example No. | 1A-1C | 3 | |
| | Time | 12-24 hrs | >24 hrs | |
| | % crystalline | <5% | 65-100% | |

The composition prepared according to the process of this invention is substantially amorphous. Such a composition contains crystalline benzimidazole compound at levels less than 30% by weight, preferably less than 5% by weight and more preferably below the limit of detection.

We claim:

1. A process for the preparation of a stable oral benzimidazole composition, the process comprising the steps of:
   a. preparing a benzimidazole core formed by dispersing one or more amorphous benzimidazole compounds and one or more pharmaceutically acceptable additives in an aqueous or hydroalcoholic medium to obtain a dispersion and spraying the dispersion on to a pharmaceutically acceptable inert carrier at a bed temperature of less than about 50° C. for a total spraying time of less than about 24 hrs;
   b. coating the core of step (a) with a separating layer; and
   c. coating the product of step (b) with an enteric coating, wherein the composition contains less than about 30% by weight of crystalline benzimidazole after storage at 40° C. and 75% relative humidity for 3 months.

2. The process according to claim 1, wherein the dispersion of step (a) is prepared in more than one lot.

3. The process according to any of the claim 1 or 2, wherein the benzimidazole compounds are selected from one or more of omeprazole, lansoprazole, rabeprazole, pantoprazole, leminoprazole, pariprazole, single enantiomers, pharmaceutically accepted salts, solvates and their mixtures.

4. The process according to claim 1, wherein the pharmaceutically acceptable additives are selected from one or more of binders, diluents, disintegrants, lubricants and wetting agents.

5. The process according to claim 1, wherein the separating layer comprises a substantially water-soluble material.

6. The process according to claim 4, wherein the binder is selected from one or more of cellulose derivatives, gums, water-soluble vinyl pyrrolidone polymers, and sugars.

7. The process according to claim 4, wherein the diluent is selected from one or more of sugars, sugar alcohols, cellulose derivatives and starches.

8. The process according to claim 4, wherein the disintegrant is selected from one or more of sodium starch glycolate, croscarmellose sodium, crospovidone and corn starch.

9. The process according to claim 4, wherein the lubricant is selected from one or more of magnesium stearate, talc, sodium stearylfumarate and colloidal silicon dioxide.

10. The process according to claim 4, wherein the wetting agent is selected from one or more of sodium lauryl sulphate and polysorbate 80.

11. The process according to claim 5, wherein the substantially water-soluble material comprises one or more of a substantially water-soluble polymer and a substantially water-soluble excipient.

12. The process according to claim 11, wherein the substantially water-soluble polymer is selected from one or more of hydroxypropyl methylcellulose, hydroxypropyl cellulose, polyvinylpyrrolidone, sodium alginate, sodium carboxymethyl cellulose and copolymer of vinylpyrrolidone and vinyl acetate.

13. The process according to claim 11, wherein the substantially water-soluble excipient is selected from one or more of lactose, mannitol, sorbitol, sucrose and glucose.

14. A process for the preparation of a stable oral benzimidazole composition, the process comprising the steps of:
   a. preparing a benzimidazole core formed by dispersing one or more amorphous benzimidazole compounds and one or more pharmaceutically acceptable additives in an aqueous or hydroalcoholic medium to obtain a dispersion and spraying the dispersion on to a pharmaceutically acceptable inert carrier at a bed temperature of less than about 50° C. for a total spraying time of less than about 24 hrs;
   b. coating the core of step (a) with a separating layer; and
   c. coating the product of step (b) with an enteric coating, wherein the composition contains less than about 5% by weight of crystalline benzimidazole after storage at 40° C. and 75% relative humidity for 3 months.

15. The process according to claim 14, wherein the dispersion of step (a) is prepared in more than one lot.

* * * * *

UNITED STATES PATENT AND TRADEMARK OFFICE
CERTIFICATE OF CORRECTION

PATENT NO. : 8,658,216 B2 Page 1 of 1
APPLICATION NO. : 11/722731
DATED : February 25, 2014
INVENTOR(S) : Rajesh Gandhi, Chayapathy Issa and Vishnubhotla Nagaprasad It is certified that error appears in the above-identified patent and that said Letters Patent is hereby corrected as shown below:

In the Specification

Column 1, line 24: "stabailize" should read -- stabilize --

Column 1, line 32: "U.S. Patent. Application No. 2003/0232861" should read -- U.S. Patent Application No. 2003/0232861 --

Column 1, line 35: "patent application No. 2003/0232861" should read -- Patent Application No. 2003/0232861 --

Column 1, line 38: "Indian application no. 1494/DEL/2003, discloses" should read -- Indian Application No. 1494/DEL/2003 discloses --

Column 2, line 14: "about 30% weight" should read -- about 30% by weight --

Column 3, line 10: "in a patent" should read -- in a patient --

Column 7, line 60: "C. Separating Layer" should read -- B. Separating Layer --

In the Claims

Column 12, line 3, Claim 3: "of the claim 1 or 2," should read -- of the claims 1 or 2, --

Signed and Sealed this
Third Day of February, 2015

Michelle K. Lee
*Deputy Director of the United States Patent and Trademark Office*